(12) United States Patent
Kang et al.

(10) Patent No.: US 9,554,895 B2
(45) Date of Patent: Jan. 31, 2017

(54) EAR SCAFFOLD

(75) Inventors: Norbert Kang, London (GB); Marie-Claire Haines, London (GB)

(73) Assignee: Northwood Medical Innovation Limited (GB)

( * ) Notice: Subject to any disclaimer, the term of this patent is extended or adjusted under 35 U.S.C. 154(b) by 0 days.

(21) Appl. No.: 14/009,196

(22) PCT Filed: Mar. 28, 2012

(86) PCT No.: PCT/GB2012/000282
§ 371 (c)(1),
(2), (4) Date: Feb. 11, 2014

(87) PCT Pub. No.: WO2012/136950
PCT Pub. Date: Oct. 11, 2012

(65) Prior Publication Data
US 2014/0228953 A1    Aug. 14, 2014

(30) Foreign Application Priority Data

| Apr. 5, 2011 | (GB) | ................................. | 1105744.5 |
| Apr. 5, 2011 | (GB) | ................................. | 1105745.2 |
| Apr. 5, 2011 | (GB) | ................................. | 1105746.0 |

(51) Int. Cl.
| A61F 2/18 | (2006.01) |
| A61F 11/00 | (2006.01) |
| A61F 2/00 | (2006.01) |
| A61B 17/34 | (2006.01) |

(52) U.S. Cl.
CPC .............. *A61F 2/18* (2013.01); *A61F 11/004* (2013.01); *A61B 17/3468* (2013.01); *A61F 2/0059* (2013.01); *A61F 2002/183* (2013.01); *A61F 2210/0014* (2013.01); *A61F 2230/0013* (2013.01)

(58) Field of Classification Search
CPC .. A61F 2002/183; A61F 2/18; A61F 13/2017; A61F 11/002; A61B 17/064; A61B 17/0644; A61B 2017/0427; A61B 17/068
USPC ......................................... 606/157
See application file for complete search history.

(56) References Cited

U.S. PATENT DOCUMENTS

| 3,174,851 A | 3/1965 | Buehler et al. |
| 5,433,748 A | 7/1995 | Wellisz |
| 5,713,947 A | 2/1998 | Davidson |
| 5,897,591 A * | 4/1999 | Kobayashi ................. 623/13.11 |
| 6,375,826 B1 * | 4/2002 | Wang et al. .................. 205/684 |

(Continued)

FOREIGN PATENT DOCUMENTS

| JP | H0737200 U | 7/1995 |
| JP | 1014971 | 1/1998 |

(Continued)

OTHER PUBLICATIONS

International Search Report for PCT/GB2012/000282, Completed by the European Patent Office on May 29, 2012, 6 Pages.

(Continued)

*Primary Examiner* — Thomas J Sweet
*Assistant Examiner* — Wade P Schutte
(74) *Attorney, Agent, or Firm* — Senniger Powers LLP (57) ABSTRACT

A scaffold for reshaping the cartilaginous portion of an ear. The scaffold is formed of shape memory material and in the form of a horseshoe shape, or is formed from a thermoplastic pliable material.

18 Claims, 6 Drawing Sheets

(56) References Cited

U.S. PATENT DOCUMENTS

| | | | |
|---|---|---|---|
| 7,182,771 B1* | 2/2007 | Houser et al. ............... | 606/155 |
| 7,799,075 B2 | 9/2010 | Kang et al. | |
| 8,157,823 B2* | 4/2012 | Aronson ............. | A61M 16/208 |
| | | | 606/157 |
| 2002/0022861 A1* | 2/2002 | Jacobs et al. ............... | 606/216 |
| 2003/0060877 A1* | 3/2003 | Falotico et al. ............. | 623/1.42 |
| 2003/0105473 A1* | 6/2003 | Miller ................. | A61B 17/064 |
| | | | 606/139 |
| 2010/0211098 A1* | 8/2010 | Hadba ............. | A61B 17/06166 |
| | | | 606/232 |
| 2012/0277770 A1* | 11/2012 | Fenton ............ | A61B 17/06166 |
| | | | 606/151 |

FOREIGN PATENT DOCUMENTS

| | | |
|---|---|---|
| WO | 03086495 | 10/2003 |
| WO | 2007023296 | 3/2007 |

OTHER PUBLICATIONS

Sorribes et al. Arch Otolaryngol Head Neck Surg. Dec. 2002, vol. 128, p. 1369-1376, "Nonsurgical Treatment of Prominent Ears With the Auri Method."

Bulstrode et al. British Journal of Plastic Surgery 2003, vol. 56, p. 145-149, "Otoplasty by percutaneous anterior scoring. Another twist to the story: a longterm study of 114 patients."

Nieminen et al. J. Mater. Sci: Mater. Med. 2008, vol. 19, p. 1155-1163, "Degradative and mechanical properties of a novel resorbable plating system during a 3-year follow-up in vivo and in vitro."

Firmin et al. Journal of Plastic, Reconstructive and Aesthetic Surgery 2008, vol. 61, p. S13-S20, "Ear reconstruction following severe complications of otoplasty."

Ullmann et al. Plastic and Reconstructive Surgery 2002, vol. 109, No. 3, p. 907-913, "Early Nonsurgical Correction of Congenital Auricular Deformities."

Iatrou et al. Oral Presentations Paediatric Maxillofacial Surgery Sep. 2006, "The use of biodegradable plates in oral and maxillofacial surgery in children."

Janz et al. Plast. Reconstr. Surg. 2009, vol. 124, p. 27e-37e, "Treatment of Prominent and Constricted Ear Anomalies."

Jeffery, British Journal of Plastic Surgery 1999, vol. 52, p. 588-590, "Complications following correction of prominent ears: an audit review of 122 cases."

Alexander et al. Journal of Plastic, Reconstructive and Aesthetic Surgery 2011, vol. 64, p. 41-47, "A morphometric study of the human ear."

Tan et al. Ann Plast Surg 1997, vol. 38, p. 263-268, "Molding Therapy for Infants with Deformational Auricular Anomalies."

Furnas, Clinics in Plastic Surgery Apr. 1990, vol. 17, No. 2, p. 305-318, "Complications of Surgery of the External Ear."

Jackson et al. NASA Publication SP5110, 1972, 96 Pages, "55-Nitinol—The Alloy with a Memory: Its physical Metallurgy, Properties, and Applications, A report."

* cited by examiner

EAR SCAFFOLD

CROSS-REFERENCE TO RELATED APPLICATION

This application is the U.S. national phase of PCT Application No. PCT/GB2012/000282 filed on Mar. 28, 2012, which claims priority to Great Britain Patent Applications Nos. GB1105744.5 filed Apr. 5, 2011, GB1105745.2 filed Apr. 5, 2011, and GB1105746.0, filed Apr. 5, 2011, the disclosures of which are incorporated in their entirety by reference herein.

FIELD OF THE INVENTION

The present invention relates to a scaffold for reshaping the ear of an animal, preferably a human, wherein the scaffold is in the form of a specified pre-programmed shape. More specifically the invention relates to a scaffold formed from shape memory material and is in the form of a horseshoe shape, or is introduced into the ear using a catheter, or is formed from a thermoplastic pliable material.

BACKGROUND TO THE INVENTION

Prominent ear deformity is common amongst the human population. An ear which projects more than 17 mm from the side of the head is usually perceived as prominent. By this estimate, up to 10% of the population may be affected [1-2]. It is desirable to correct the prominence very early in life when the cartilage is soft and pliable, however often the prominence is ignored and not treated. Consequently, many children suffer the psychological consequences associated with prominent ears which can persist into adulthood. Therefore there is a need to develop a safe and effective method for correction which can be used in both adults and children.

Figure 1A:
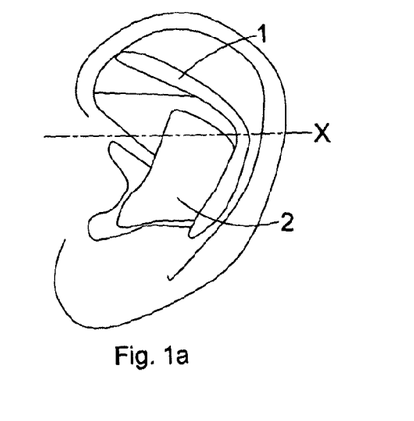
FIG. 1a is a schematic front view of the ear showing the antihelical fold (1) and the conchal fossa (2)
Figure 1B:
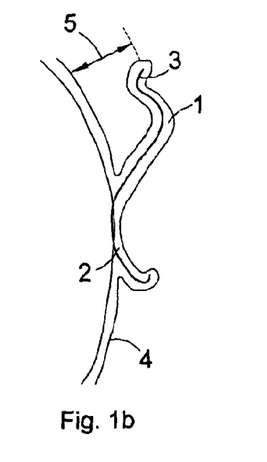
FIG. 1b is a cross section (X) of the diagram of FIG. 1a additionally showing the cartilaginous portion and the distance between the cartilage (3) and skin (4) which is normally in the range of 15-17 mm (5)
Figure 2A:
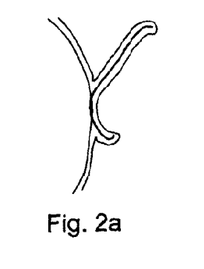
FIG. 2a shows a cross section diagram of an ear where the antihelical fold is absent or poorly formed.
Figure 2B:
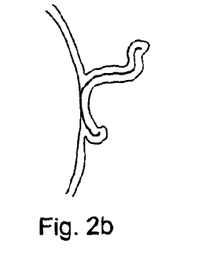
FIG. 2b shows a cross section diagram of an ear with a deep conchal fossa.

The ear cartilage is cup-shaped and is formed of the conchal fossa and the antihelical fold which allows the ear to lie flat against the side of the head. Prominence may result in the abnormal formation of the antihelical fold, or folded over rim (FIGS. 1b and 2a) during embryonic development. Alternatively, it may be the result of a deep conchal fossa (FIG. 2b). One or both of these abnormalities may need to be addressed when correcting prominence of the ear. However, even for ears with a deep conchal bowl, accentuation of the antihelical fold will make a difference to the perception of prominence[1]. In most cases the prominence is apparent at birth but can develop soon afterwards and in some cases up to the age of five.

There are a number of known methods for addressing the problem of prominent ears such as otoplasty surgery and non-invasive methods involving the application of devices or splints to the exterior of the ear.

Surgical techniques, for example otoplasty or pinnaplasty, are available to change the shape of the ear and correct the deformity. These vary from very invasive procedures to reshape the cartilage to minimally invasive procedures, for example percutaneous scoring of the cartilage[3]. The principle involved in all of these procedures is reshaping of the cartilage which gives the ear its prominence. However, otoplasty is a lengthy procedure taking approximately 45 minutes for each ear. In addition a number of problems and complications are associated with this type of surgery and with percutaneous scoring of the cartilage[3-6] such as infection, bleeding, skin necrosis, death from general anaesthesia, recurrence of the prominence, keloid or hypertrophic scarring, asymmetry, palpable sharp edges (where the cartilage has been cut), pain, numbness and cold intolerance/sensitivity.

The use of minimally invasive techniques using needles or similar instruments overcome some of the above-identified problems, have fewer complications and take less time, for example 15 minutes per ear. However, such techniques have the disadvantage in that they are less successful in achieving the desired prominence correction and have a higher rate of asymmetry and the formation of palpable sharp edges compared with standard otoplasty surgery.

Furthermore such surgical techniques, both invasive and minimally invasive, require substantial training and experience. In general the results of the first 10-20 cases are likely to be unpredictable [6]. To overcome the problems associated with surgical otoplasty and minimally invasive methods several known devices are in use to correct the deformity and avoid surgery altogether. These are essentially external splints which deform the cartilage by the continuous application of external force.

One such device, known as Earbuddies™ is formed from a piece of soft wire coated in silicone (for comfort) which is moulded and placed onto the outside of the ear and taped into position. The cartilage moulds its shape to that of the ear buddy and any prominence is corrected. At birth and for a variable time afterwards (up to six months), the cartilage of the human ear remains soft and deformable. Therefore, external forces applied to the cartilage can result in permanent changes to its shape[7-8]. Hence, Earbuddies™ have most success in children up to the age of six months, after this age the cartilage becomes firmer and more resistant to deformation. Also the increasing dexterity of the child who will try (and usually succeed) in removing the splint reduces its effectiveness.

Another device, Aurimethod™ which includes the use of the Auri®Clip and Auri®Strip devices applies gentle, continuous, external pressure to the cartilage of the ear in the region of the antihelical fold. This deforms the cartilage in this area over a prolonged period of time to make the ears lie flatter against the head. The Auri®Strip is a very thin (0.2 mm thick), transparent and double-sided medical adhesive material that is invisible when worn and can also be used to reshape the antihelical fold. It is claimed that 3 to 6 months treatment is enough to have a permanent effect.

The disadvantage of this method is skin irritation and compliance which reduced the overall success rate [9].

Figure 3A:
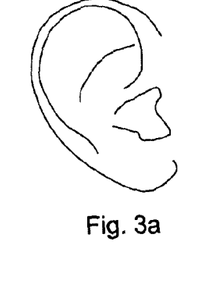
FIGS. 3a, 3b and 3c show schematic front view diagrams of an ear showing scaffolds being positioned.
Figure 3B:
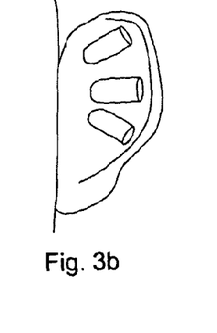
Figure 3C:
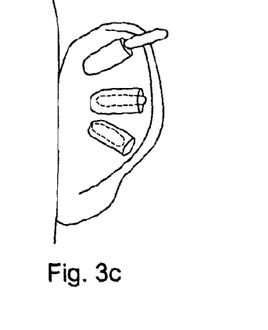

WO2007/023296 discloses surgical scaffolds formed of shape memory material for use in reshaping the cartilage of the nose or the ear. One, two (or three) of the implants (FIG. 3) are inserted subcutaneously into the ear as shown in FIG. 3c. On insertion, the implant is embedded in the cartilage and released. Upon release, the implant changes from one shape to a second pre-programmed shape which results in an instant change in the shape of the underlying cartilage.

These scaffolds have a reduced risk of complications and time taken to recover from the treatment and have therefore overcome a number of the problems associated with standard otoplasty and minimally invasive otoplasty surgery. However, such devices often do not produce the desired change in shape of the anti-helical fold and although the anti-helix does fold, it is not always in a predictable manner to produce the optimal curvature. In addition these scaffolds often have a poor conformance to the cartilage and sit 'proud' which can compromise the correction of prominence. Therefore there is a need to further improve the attachment and fit of the scaffold to the cartilage to achieve reliable results.

Furthermore these scaffolds are designed to fit the average dimensions of the human ear, and as such are not suitable for all ears which are infinitely variable. Furthermore, there is a need to improve design and materials such that insertion and removal are minimally invasive.

Due to the size of the introducer on which the scaffold is held, it is necessary to make a corresponding incision that will accommodate the introducer such that the scaffold can be correctly positioned in place. This has the disadvantage that recovery time is longer due to post-surgical effects such as pain and bleeding. In addition, further surgical intervention is necessary to remove the scaffold once correction has been effected due to the visibility of the scaffold under the skin. Also, these scaffolds are not suitable for long term or permanent use.

Whilst the suitability of Nitinol scaffolds has been established for use in correcting ear deformities there remains a need to further improve the design of the scaffolds such that insertion and removal are minimally invasive and the method of insertion is simpler requiring less time and surgical skill. In addition, a design with lower visibility has the advantage that removal is not necessary in cases where deformity is not permanently corrected after treatment, or if the scaffold is to be removed, this will be required less often.

Thermoplastics are polymers capable of undergoing a reversible transition from a relatively hard brittle state to a molten or rubber-like state. The temperature at which this occurs is known as the glass transition temperature (Tg). Thermoplastics can undergo repeated melting/cooling cycles and can be re-shaped on heating. Known thermoplastics include polyethylene, polypropylene, polystyrene, polyester, polyvinyl chloride, acrylics, nylons, spandex-type polyurethanes and cellulosics.

The thermoplastic polymers manufactured by Inion Oy, Finland, have been used successfully in bone regeneration[10] and are biodegradable. The polymers degrade in vivo by hydrolysis within 12 months to form carbon dioxide and water[11]. The polymers are commercially available in the form of pre-cut strips or as plates from which the desired shape and size can be easily cut.

It is an object of the present invention to provide an improved ear scaffold which overcomes the above-mentioned problems and demonstrates improved predictability and efficacy.

SUMMARY OF THE INVENTION

The inventors have devised a scaffold formed from shape memory material which is in the shape of a horseshoe.

The inventors have devised an improved scaffold which addresses the above problems and can be inserted using a catheter as a conduit in a minimally invasive manner.

The inventors have devised a mouldable ear scaffold which can be shaped such that correction is specific for the individual requirements of the patient. Furthermore, as the scaffold is biodegradable no additional surgery is necessary to remove the scaffold once correction has been effected. Therefore, a biodegradable scaffold has the advantage that it can be inserted and left in situ with no requirement for a follow-up consultation and/or removal.

According to a first aspect of the present invention there is provided a scaffold for reshaping the cartilaginous portion of an ear, the scaffold being formed from shape memory material characterised in that the scaffold is in the shape of a horseshoe.

According to a further aspect of the present invention there is provided a scaffold for reshaping the cartilaginous portion of an ear, the scaffold being formed from shape memory material characterised in that the scaffold is made of wire and is inserted into the ear using a catheter.

According to a further aspect of the present invention there is provided a scaffold for reshaping the cartilaginous portion of an ear, the scaffold being formed from a thermoplastic mouldable material.

According to a further aspect of the present invention there is provided an applicator for inserting the scaffold when formed of shape memory material into the cartilaginous portion of the ear comprising a retaining means.

According to a further aspect of the invention when the scaffold is in the form of a wire there is provided an applicator for inserting the scaffold into the cartilaginous portion of the ear.

According to a further aspect of the present invention there is provided a method of treatment for reshaping the ear using the scaffold, comprising the steps of inserting at least one scaffold into the ear to be corrected, wherein the scaffold transforms from a first configuration to a second pre-programmed configuration, wherein the second pre-programmed configuration is in the shape of a horseshoe.

According to a further aspect of the invention when the scaffold is in the form of a wire there is provided a method for re-shaping the ear, comprising the steps of inserting a scaffold into the ear to be corrected using a catheter wherein the scaffold transforms from a first configuration to a second pre-programmed configuration.

According to a further aspect of the invention when the scaffold is formed of a thermoplastic pliable material, there is provided a method for reshaping the ear using the scaffold of the invention. The method may comprise moulding the scaffold in vivo such that heat is applied to the scaffold once inserted into the sub dermal layer or moulding the scaffold prior to insertion in the sub dermal layer.

The term "scaffold" as used herein is any structure or framework which may be used to reshape an ear. Preferably upon implantation into the patient the scaffold does not adversely react with the patient.

The term "horseshoe" as used herein means a substantially U shape comprising tangent lengths, or tangential extensions. The horseshoe may be in a configuration whereby the tangent lengths are tapered. Alternatively the horseshoe may be in a configuration whereby the tangent lengths are in a parallel arrangement. In either case the tangent lengths may be of varying length.

The term "catheter" can be defined as a hollow tube that can be inserted into a body cavity, duct or vessel. The catheter may be made of any suitable material.

The term "shape memory material" is well known in the art and may be defined as a material which is capable of transforming from a first configuration to a second pre-programmed configuration. This may be initiated by a change in temperature. A nickel and titanium alloy such as Nitinol is an example of a shape memory material.

The term "thermoplastic" as used herein refers to a polymer which changes from a rigid state to a flexible, pliable state upon exposure to heat and re-hardens on cooling without a change in other properties.

BRIEF DESCRIPTION OF THE DRAWINGS

The present invention will now be described further by way of example with reference to the drawings.

The first and/or second configuration of the scaffold may be in a constrained or non-constrained state. The first configuration may be in the constrained state and the second configuration may be in the non-constrained state.

DETAILED DESCRIPTION OF THE INVENTION

The scaffold adopts the pre-programmed shape when in the second configuration.

The scaffold may be configured to adopt a substantially curved form when in the pre-programmed shape and a substantially straight form when in the first configuration. The scaffold may be configured to conform to the shape of an antihelical fold of an ear or the conchal fossa of an ear when in the pre-programmed shape. For example, the scaffold is configured to conform to the shape of an antihelical fold of an ear when in the pre-programmed shape.

When the scaffold is made of wire it may comprise a proximal and distal portion and may be configured to adopt symmetrical or asymmetrical confirmations when in the pre-programmed shape. For example, the distal and proximal portions of the scaffold may be configured asymmetrically. The scaffold may be larger at the distal end and smaller at the proximal end. In one embodiment, the larger portion may be substantially circular in shape, and the smaller portion may be elongated. Alternatively, the smaller distal portion may also be circular. In this arrangement the distal portion may be positioned in the cartilaginous region of the ear and the proximal portion in the antihelical fold region. A scaffold comprising a larger distal portion provides enhanced deflection of the antihelical fold when in its pre-programmed shape.

Alternatively, the distal and proximal portions of the scaffold may be configured symmetrically. In one example the distal and proximal portions of the scaffold are the same size and shape. In a further example both the distal and proximal portions are substantially circular in shape.

The scaffold may be formed of shape memory material and is capable of transforming from a first configuration to a second pre-programmed configuration wherein the second pre-programmed configuration is in the shape of a horseshoe.

When the scaffold is formed of a thermoplastic material, the material is capable of transforming from a rigid state to a flexible state when exposed to elevated temperatures. The thermoplastic material may be comprised of trimethylene carbonate, L-Lactide and D-Lactide, and polyglycolide. The proportions of trimethylene carbonate, L-Lactide, D, L-Lactide and polyglycolide may vary. For example, the proportions of trimethylene carbonate, L-Lactide and D-Lactide, and polyglycolide are varied to provide polymers with differing thermoplastic and biodegradability properties.

The scaffold transforms from a rigid state to a flexible, pliable state at temperatures above 55° C., although transformation may be at temperatures above 65° C. or 85° C. but not exceeding 100° C. Typically, the scaffold transforms from a rigid state to a flexible, pliable state within a temperature range of 85° C. to 95° C.

The transformation of the scaffold from a rigid state to a flexible state by a change in temperature may be effected by any means. In one embodiment the change in temperature is effected by immersing in water at a defined temperature.

The scaffold may adopt a flexible state for a variable length of time depending on the relative proportions of trimethylene carbonate, L-Lactide, D, L-Lactide and polyglycolide. For example the scaffold is flexible for at least 5 seconds. In a further example the scaffold is flexible for 10 to 20 seconds.

The scaffold may be biodegradable when formed of thermoplastic material. The time taken for the scaffold to degrade may vary. For example the scaffold degrades after six months. In another example the scaffold degrades after 12 months.

Figures 4A, 4B, 5:
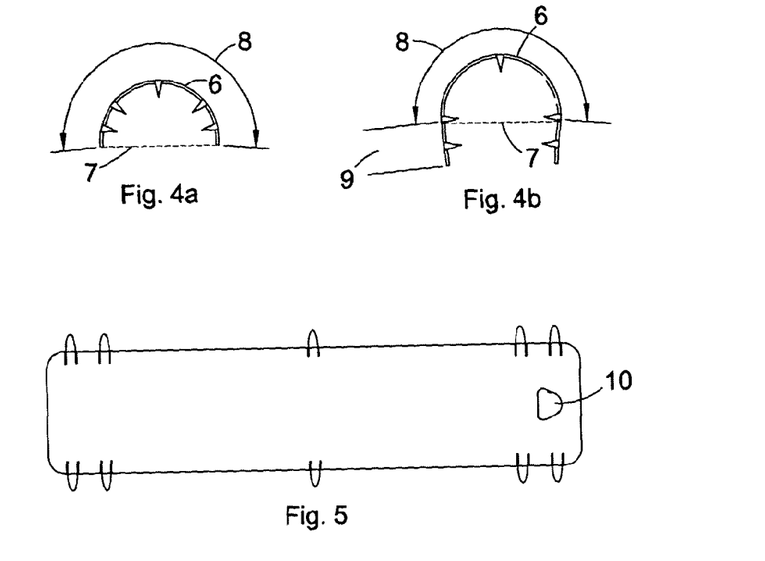
FIG. 4a shows a scaffold in its first pre-programmed position in the shape of a semi-circle.
FIG. 4b shows a scaffold is its first pre-programmed configuration, comprising tangential extensions, in the shape of a U or horseshoe.
FIG. 5 is a schematic upper view of the scaffold showing the position of the opening.

FIG. 4 shows the scaffold (6) in its second pre-programmed configuration in the shape of a semi-circle (FIG. 4a) or horseshoe (FIG. 4b). The radius of curvature (7) is the radius between the surfaces of the scaffold at its widest point, when in its second pre-programmed configuration. The radius of curvature of the scaffold is at least 3 mm, although it may be 4 mm or 5 mm or even up to 6 mm. The bend angle (8) is typically in the range of 185° to 195°.

The shape of the scaffold in its pre-programmed position determines the degree of curvature of the anti-helical fold. The inventors have found that the presence of a tangential extension (9) results in greater deflection of the anti-helical fold and therefore an enhanced curvature. The degree of curvature of the anti-helical fold is determined by the compression force exerted by the scaffold in its pre-programmed position. A scaffold in the shape of a horseshoe in its pre-programmed position exerts a higher compression force and thus provides greater deflection and an enhanced curvature. The greater compression force exerted by the scaffold in this conformation also prevents opening or widening of the ends of the scaffold which can occur as a consequence of the natural elasticity of the cartilage rebounding into its original form. Therefore, the higher compression forces exerted by the horseshoe shape provide for greater deflection, enhanced curvature and also enable the scaffold to retain its pre-programmed configuration and withstand the natural elastic forces of the cartilage. In addition the horseshoe shape provides for an improved attachment of the scaffold to the cartilage due to the presentation of the tines in an orientation that grips the cartilage more effectively and therefore reduces the likelihood of the scaffold slipping out of the cartilage. This is caused by the angle and the direction of the forces being applied to the tines in relation to the force being generated by the implant. For example the angle of the tines is closer to 90° in respect of the horseshoe scaffold compared to approximately 45° with the semi-circular scaffold when embedded in the cartilage.

The scaffold comprises tangential extensions. The tangential extensions of the horseshoe may point inwards. The tangent length is at least 1 mm although it may be 2 mm or 3 mm or even up to 5 mm long. For example the tangent length is 2.3 mm.

The dimensions of the scaffold may vary. The scaffold is at least 10 mm although it may be 15 mm or 25 mm or even up to 35 mm long. The width of the scaffold is at least 1 mm although it may be 2 mm or up to 5 mm wide. The thickness is typically in the range 0.14 mm to 0.15 mm although it may be up to 2 mm. For example the scaffold is 17.9 mm long, 5 mm wide and has a thickness in the range of 0.14 mm to 0.15 mm. In a further example the scaffold is 21.2 mm long, 5 mm wide and has a thickness in the range of 0.14 mm to 0.15 mm. Alternatively the scaffold is 24.5 mm long, 5 mm wide and has a thickness in the range of 0.14 mm to 0.15 mm. If the scaffold is too thick the rigidity in relation to the cartilage can cause tearing in the event of an external force or blow to the ear. If the scaffold is too thin it lacks the capacity to effect a change in shape. The inventors have found that when the scaffold is from 0.14 mm to 0.15 mm thick and 5 mm wide the ideal elasticity and flexibility of the shape memory material is obtained.

In one example the scaffold has a length of at least 15 mm and does not exceed 25 mm, has a width of at least 2 mm and does not exceed 5 mm, has a thickness in the range of 0.14 mm to 0.15 mm and has a tangent length of 2.3 mm.

In another example the scaffold has a length of at least 10 mm but not more than 35 mm, a width of at least 1 mm but not more than 5 mm and a thickness in the range 0.14 mm to 0.15 mm and has a tangent length of 2.3 mm.

In a further example the scaffold has a length of 14.8 mm, a width of 5.0 mm and a thickness of 0.15 mm and has a tangent length of 2.3 mm.

The scaffold may have a thickness below 0.14 mm, for example in the range 0.11 mm to 0.14 mm. In one embodiment the scaffold has a thickness of 0.13 mm. A scaffold with a thickness below 0.14 mm has greater elasticity and is less stiff resulting in a scaffold that forms a more gentle curve when in its second pre-programmed configuration. This has the advantage that the scaffold may be applied to parts of the ear where a more subtle correction is required. In one example the scaffold is 17.9 mm long, 5 mm wide and has a thickness in the range of 0.11 mm to 0.14 mm. In a further example the scaffold is 21.2 mm long, 5 mm wide and has a thickness in the range of 0.11 mm to 0.14 mm. Alternatively the scaffold is 24.5 mm long, 5 mm wide and has a thickness in the range of 0.11 mm to 0.14 mm.

In one example the scaffold has a length of at least 15 mm and does not exceed 25 mm, has a width of at least 2 mm and does not exceed 5 mm, has a thickness in the range of 0.11 mm and 0.14 mm and has a tangent length of 2.3 mm.

In another example the scaffold is 14.8 mm long, 5 mm wide and has a thickness of 0.13 mm.

When the scaffold is made of wire the length of the scaffold is at least 10 mm although it may be 15 mm or 25 mm or even up to 35 mm long. The width of the scaffold may be at least 1 mm, although it may be 2 mm or up to 5 mm wide. The diameter of the wire is at least 0.1 mm, although it may be 0.4 mm or 0.5 mm, or even up to 0.6 mm. The diameter of the wire is typically in the range of 0.4 mm to 0.6 mm. For example, the scaffold is 17.9 mm long, 5 mm wide and the diameter of the wire is in the range 0.4 mm to 0.6 mm. In a further example the scaffold is 24.5 mm long, 5 mm wide and the diameter of the wire is in the range of 0.4 mm to 0.6 mm.

If the wire of the scaffold is too thick, the rigidity with respect to the cartilage can cause tearing of the tissues in the event of an external force or blow to the ear. If the wire of the scaffold is too thin it lacks the capacity to effect a change in shape. The inventors have found that when the wire of the scaffold is from 0.4 mm to 0.6 mm in diameter the ideal elasticity and flexibility of the shape memory material is obtained.

In one example of the invention, the scaffold has a length of at least 15 mm and does not exceed 25 mm, has a width of at least 2 mm and does not exceed 5 mm, has a wire diameter of at least 0.2 mm and does not exceed 0.6 mm and has a tangent length of 2.3 mm.

When the scaffold is formed of a thermoplastic pliable material the dimensions of the scaffold may vary depending on the ear dimensions of the patient to be treated. The scaffold is at least 10 mm long, although it may be 15 mm or 25 mm or even up to 35 mm long. The width of the scaffold is at least 1 mm although it may be 2 mm or up to 5 mm wide. The thickness of the scaffold is at least 0.5 mm, although it may be 1.0 mm or up to 1.5 mm thick. For example, the scaffold is between 15 mm to 25 mm long, 5 mm wide and has a thickness in the range 0.5 mm to 1.5 mm. In a further example the scaffold is 24.5 mm long, 5 mm wide and has a thickness in the range 0.5 mm to 1.0 mm.

Once the prominence is corrected it is necessary to remove the scaffold from the ear. It is desirable to remove the scaffold without causing further trauma and damage to the surrounding tissues. The scaffold may be removed from the ear by grabbing an end of the scaffold with a suitable device and pulling. Alternatively, the scaffold (FIG. 5) may comprise an opening (10) at one end to allow removal by a device with means for attaching to the scaffold via the opening. In a further embodiment of the present invention the scaffold comprises openings at one or both ends. For example the scaffold comprises an opening at one end.

Figure 6:
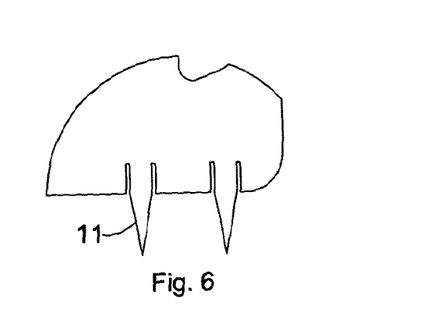
FIG. 6 shows a schematic diagram of a portion of a scaffold detailing the shape and dimensions of the tines.

The scaffold optionally comprises one or more engaging members to attach to the cartilaginous portion of the ear (FIG. 6). The engaging members may be in the form of spikes, prongs, tines or cylindrical or branched protrusions. For example the engaging members are in the form of tines (11).

The engaging members are positioned on each edge of the scaffold in a parallel arrangement.

The engaging members may be positioned along the length of the scaffold, or in irregular pre-defined positions. For example the majority of engaging members are positioned at the ends of the scaffold.

In one embodiment the engaging members are positioned slightly inwards from the edge of the scaffold. The engaging members may be positioned 1 mm from the edge of the scaffold. This has the advantage that the edges of the scaffold can be more easily rounded.

The number of engaging members on the scaffold may be varied. For example the scaffold will have at least 8 engaging members. In a further example the scaffold will have 10 engaging members. When the scaffold is made of wire the scaffold will have at least 2 engaging members.

Figure 7A:
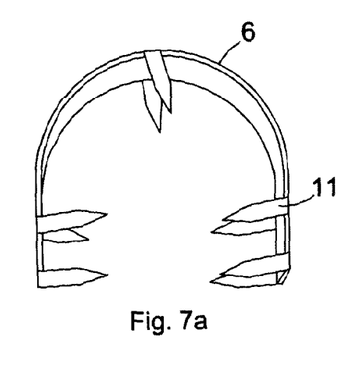
FIG. 7 shows a schematic diagram of the scaffold with the preferred positions of the tines in parallel arrangement.
Figure 14:
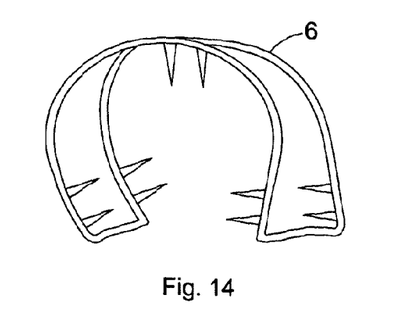
FIG. 14 shows a schematic diagram of the wire scaffold with the preferred positions of the tines in parallel arrangement.

In one embodiment the scaffold will have four engaging members positioned at the ends of the scaffold on each edge and two engaging members positioned in the centre of the scaffold on each edge of the scaffold (FIG. 7a) and shown in FIG. 14 when the scaffold is in the wire form. The inventors have found that this particular arrangement provides an improved conformation of the scaffold to the cartilage.

Figure 7B:
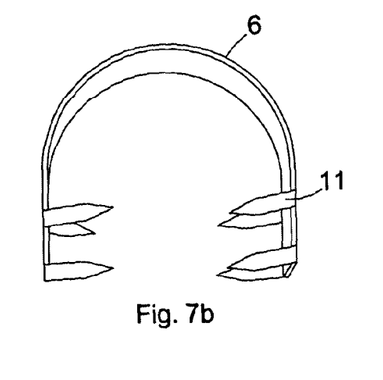

In a further embodiment the scaffold has four engaging members positioned at the ends of the scaffold on each edge. (FIG. 7b)

In a further embodiment, when the scaffold is made of wire two engaging members are positioned at the distal end of the scaffold. This has the advantage that the scaffold is less likely to dislodge once in position, and allows the scaffold to expand into the sub-dermal layer thereby forming an "interference fit".

The engaging members may have the same length and/or width as the other engaging members. Alternatively, the length and/or width of the engaging members may vary. For example all the engaging members will be of equal length and/or width. The inventors have found that this particular arrangement provides an improved confirmation of the scaffold to the cartilage.

The engaging members have a length of at least 1.0 mm although it may be 1.04 mm, or even up to 1.2 mm. For example, the length of the engaging members is 1 mm.

The engaging members may have a length below 1.0 mm. For example the length of the engaging members is in the range of 0.95 mm to 1.0 mm. In a further example the length of the engaging members is 0.96 mm.

The engaging members have a width typically in the range of 0.35 mm to 0.4 mm, for example the width is 0.4 mm.

The inventors have found that when the engaging members have a length of 1.04 mm and width of 0.4 mm the scaffold is able to sit flush to the cartilage whilst penetrating sufficiently to remain in position. It is important that the scaffold sits flush to the cartilage to allow for enhanced conformation and curvature, therefore the precise dimensions of the engaging members are directly related to the overall functionality of the scaffold.

The engaging members may be triangular in shape. The triangular or "dagger" shape allows the engaging members to penetrate and grip the cartilage sufficiently. It has been found that if the engaging member is too wide then the cartilage is not sufficiently gripped. The sharp ends of the engaging members bend slightly inwards on penetrating the cartilage, and therefore a firmer grip is achieved. In one embodiment the engaging members are tines and are triangular in shape.

Figure 8:
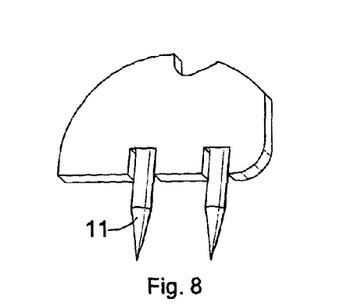
FIG. 8 shows a three dimensional diagram of a portion of a scaffold detailing the tines in a cylindrical shape.

The three dimensional shape of the engaging members may be substantially flat as shown in FIG. 7. Alternatively the three dimensional shape of the engaging members may be cylindrical (FIG. 8). In this embodiment the diameter of the engaging member at its base is at least 0.2 mm, although it may be 0.3 mm or 0.5 mm and even up to 1 mm. The inventors have found that when the engaging member is cylindrical, penetration of the cartilage is improved and further damage to the cartilage subsequent to implantation, such as tearing, is avoided.

In one embodiment the engaging members are tines and are cylindrical in shape.

When the scaffold is formed of a thermoplastic pliable material the engaging members may be formed of a different material to the scaffold. For example the engaging members are formed of a thermoplastic biodegradable material. In a further example the engaging members are formed of a thermoplastic biodegradable material which transforms to a flexible state at a higher temperature than the temperature at which the scaffold transforms to a flexible state. This has the advantage that the engaging members remain rigid when the scaffold is flexible to allow the scaffold to be fixed in position.

Figure 15:
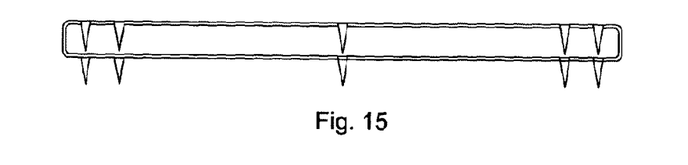
FIG. 15 shows a schematic diagram of the wire scaffold compressed along its width in its first configuration.

When the scaffold is made of wire, in one embodiment the scaffold does not comprise engaging members. In this form the scaffold is able to expand into its pre-programmed configuration and form an interference fit between the cartilage and sub-dermal layer. Thus, the scaffold is held securely in position by the overlying skin. FIG. 15 shows the scaffold in its first configuration compressed along its width, prior to insertion into the catheter. The scaffold may be compressed along its length or width. For example, the scaffold is compressed along its width. Alternatively the scaffold may be compressed by rolling along its width prior to insertion into the catheter.

The shape memory material of the present invention may be a metal alloy or a shape memory polymer.

The alloy used may be a shape memory alloy of nickel and titanium. For example the alloy comprises approximately 50% nickel and 50% titanium by weight of total composition.

The nickel titanium alloy used in the present invention is of the type disclosed in U.S. Pat. No. 3,174,851, which is known as "Nitinol". Details of such materials can be found in NASA Publication SP 5110 entitled "55-NITINOL"— The Alloy with a Memory, Its Physical Metallurgy, Properties, and Applications. C. M. Jackson et al, 1972. Many other materials having similar characteristics are well known to those skilled in the art.

The property of Nitinol which may be exploited in the present invention is the ability to pre-program a particular shape into the metal alloy and to activate the "memory" of this shape by heating/cooling it to specific temperatures. Using this property, it is possible to control the point at which the Nitinol changes shape to within from 1 to 10° C., or within from 1 to 5° C. and in one embodiment within from 1-2° C. The temperature range over which the scaffold changes from the first to the second and/or the second to the first configuration may be narrow.

In one embodiment of the present invention it is advantageous for the scaffold to have a substantially smooth surface. This allows the scaffold to be easily deployed and removed from the ear. This is achieved by polishing, electropolishing or passivating. For example this is achieved by passivating or electropolishing. This process is well known in the art and uses an electrochemical process to polish, passivate and deburr metal to give a smoother, cleaner and more biocompatible surface. For example the scaffold is passivated or electropolished. In a further example the scaffold is passivated.

The scaffold may be gold plated. This provides the advantage that the scaffold is less visible when in position underneath the skin and improves radiopacity. In one embodiment the scaffold is gold plated after passivating, electropolishing or polishing. In a further embodiment the thickness of the gold layer does not exceed 4 microns. This ensures that the elastical properties of the nitinol scaffold are not compromised.

The scaffold may be anodised to harden and colour the surface of the scaffold without altering the mechanical properties of the scaffold. The process of anodising causes the oxide layer of the surface of the metal to be adjusted resulting in changes to the spectrum of light and perceived colour. In one example the scaffold may be anodized after passivating.

The scaffold of the present invention may comprise a plastic material which may be thermoplastic and/or biodegradable.

The scaffold may comprise a plastic material which is biodegradable and/or bioabsorbable elastomer with shape memory properties. Examples of such materials may be found in Medical Device Technology, April 2005. Examples of bioabsorbable materials include, but are not limited to, poly(ε-caprolactone)diol, or those based on crystallisable macrodiols, which may be synthesised from poly(p-dioxanone)diols and poly(ε-caprolactone)diol.

Examples of bioabsorbable materials which may be used in the present invention include, but are not limited to, synthetic materials such as polyacetic acid, polyglycolic acid, polydioxanone, polytrimethylene carbonate, poly(ethylene carbonate), polyiminocarbonates), polycaprolactone, polyhydroxybutyrate, polyalkylene oxalates, polyalylene succinates, poly(maleic acid), poly(1,3-propylene malonate), poly(ethylene terephthalate), poly(amino acids) and VICRYL™ (a bioabsorbable copolymer of glycolide and lactide). For example the bioabsorbable material is a polydioxanone homopolymer. It will be understood that the selection of a suitable absorbable material will depend on such factors as the desired in vivo strength properties and absorption rate required for the scaffold.

For example the plastic material is a biodegradable "smart polymer". "Smart polymers" are well known to those skilled in the art and respond to changes in the environment and surroundings.

In a separate embodiment of the present invention the scaffold may be substantially rigid and comprised of material which does not have shape memory properties. Scaffolds comprised of rigid materials overcome the handling problems observed with shape memory materials and allow the scaffold to be pre-fabricated to the required form prior to deployment. The scaffold may be comprised of a biocompatible or bioabsorbable material as described herein. In one example the scaffold retains a degree of flexibility and elasticity. Typically, the scaffold comprises engaging members as described herein.

Figure 9A:
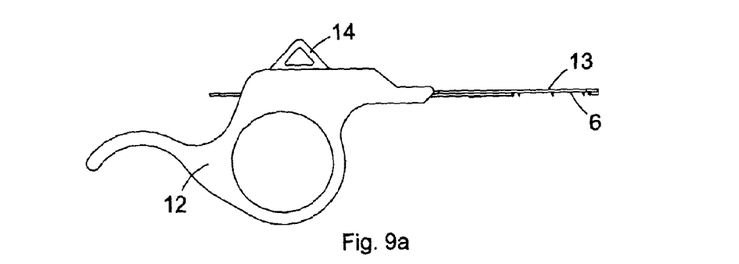
FIG. 9a shows a cross section diagram of the applicator for inserting the scaffold into the ear with the scaffold attached.
Figure 9B:
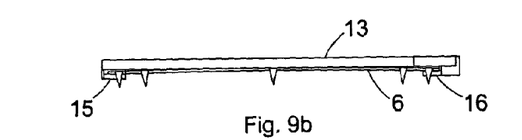
FIG. 9b shows an enlargement of the portion of the applicator with the scaffold held in its first constrained configuration.
Figure 9C:
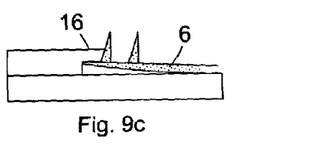
FIG. 9c shows an enlarged cross section of the distal lip holding the scaffold in its first constrained position.

In a further aspect of the present invention there is provided an applicator (FIG. 9a) for inserting the scaffold when formed of shape memory material into the cartilaginous portion of the ear comprising a retaining means (FIGS. 9b and 9c).

Figure 10:
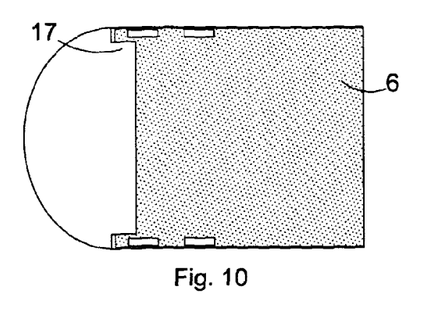
FIG. 10 shows a view from underneath of the distal lip, with notches holding the scaffold in its first constrained position.

The applicator comprises a handle (12) a retaining means (13) on which the scaffold (6) is placed prior to insertion and a slider (14) to deploy the scaffold. The retaining means holds the scaffold in its first configuration and is in the form of a proximal (15) and distal lip (16) comprising a milled edge which partially encloses the edge of the scaffold. The length of the milled edge is up to 0.6 mm, although it is typically in the range of 0.45 mm to 0.5 mm. The thickness of the milled edge is up to 0.5 mm although it is typically in the range of 0.25 mm to 0.3 mm. For example, the milled edge is 0.5 mm long and between 0.25 mm to 0.3 mm thick. Lips of a particular length improve the alignment of the scaffold with the applicator when it is in its first configuration such that contact between the scaffold and the applicator is continuous along most of the length of the scaffold. This has the effect that the scaffold can be attached to the cartilage with greater precision by ensuring that the tines engage with the cartilage before the scaffold is deployed. The lips further comprise notches (17) on the sides to prevent sideways yawing of the scaffold while it is held in the applicator as shown in FIG. 10.

Figure 9D:
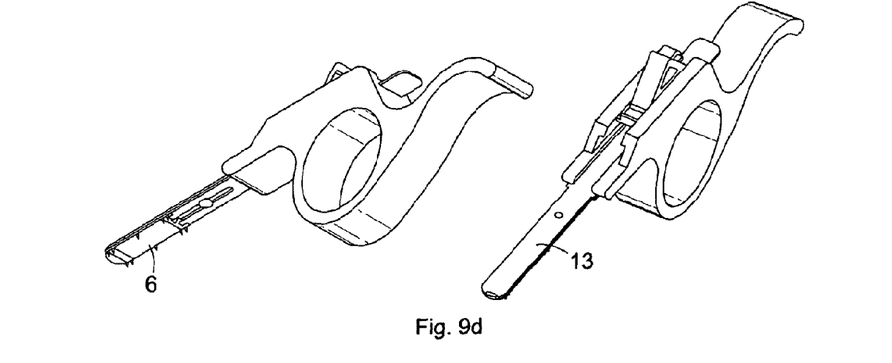
FIG. 9d shows a view of the applicator from below with the scaffold held in its first constrained configuration and, the applicator viewed from above showing the arrangement of the slider.
Figure 11A:
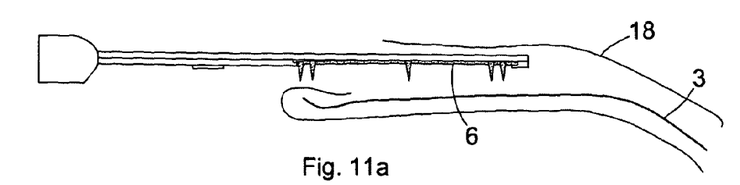
FIG. 11a-11c is a series of schematic diagrams showing insertion, positioning and release of the scaffold in the cartilaginous portion of the ear. In these diagrams the applicator is depicted in a simplified form for clarity of the diagrams and does not represent a design for use.
Figure 11B:
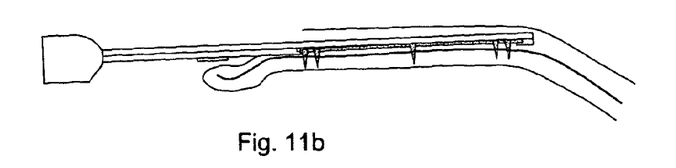
Figure 11C:
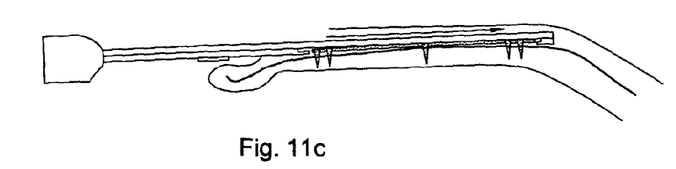
Figure 11D:
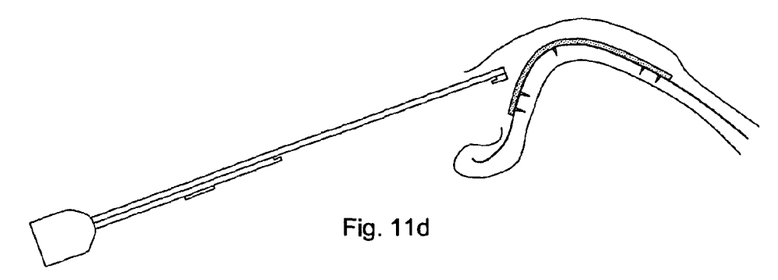
FIG. 11d shows the scaffold on position and in its second pre-programmed position.

The handle is designed such that a finger may be inserted through the handle to grip the applicator. The slider (14) to deploy the scaffold is positioned on the applicator as shown in FIGS. 9a and 9d. The slider is positioned such that it fits into the proximal and distal lip (15, 16) formed by the retaining means. The slider can be moved manually along the length of the proximal and distal lip (15, 16) causing the scaffold to be released from the retaining means and deployed. The scaffold can be inserted using the applicator as shown in FIG. 11a by placing in the subcutaneous space (18) in the desired position, and pressing into the cartilage (3) (FIG. 11b). The scaffold is released from the retaining means (FIG. 11c) and the applicator is removed leaving the scaffold securely in position (FIG. 11d). The shape of the ear is modified upon the scaffold adopting its second pre-programmed configuration as shown in FIG. 11d and FIG. 12b.

Figure 13:
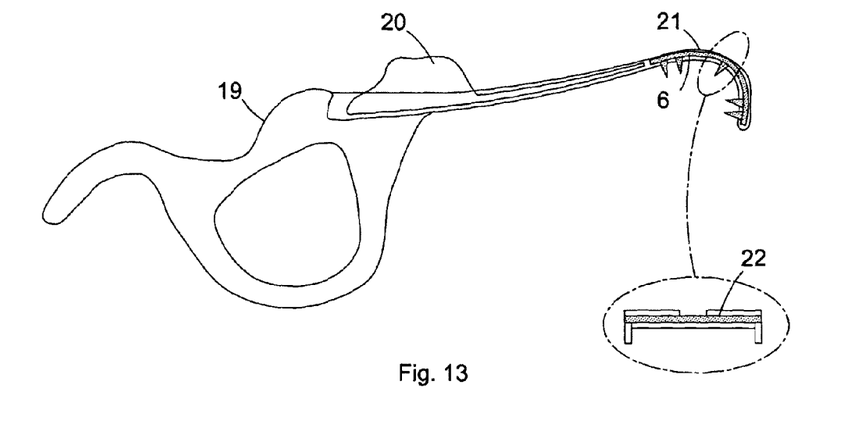
FIG. 13 shows a cross section of an applicator used for positioning a rigid scaffold.

In another aspect of the invention rigid scaffolds may be inserted using a specifically designed applicator (FIG. 13). The applicator comprises a handle (19) a flexible slider (20) and a curved portion (21) for retaining the scaffold (6) prior to insertion. The curved portion (21) comprises means for partially enclosing the scaffold (6). The scaffold is released by moving the flexible slider (20) forwards thereby deploying the scaffold (6) in the desired position.

In a further aspect of the invention when the scaffold is in the form of a wire there is provided an applicator (FIG. 16) for inserting the scaffold into the cartilaginous portion of the ear.

Figure 16:
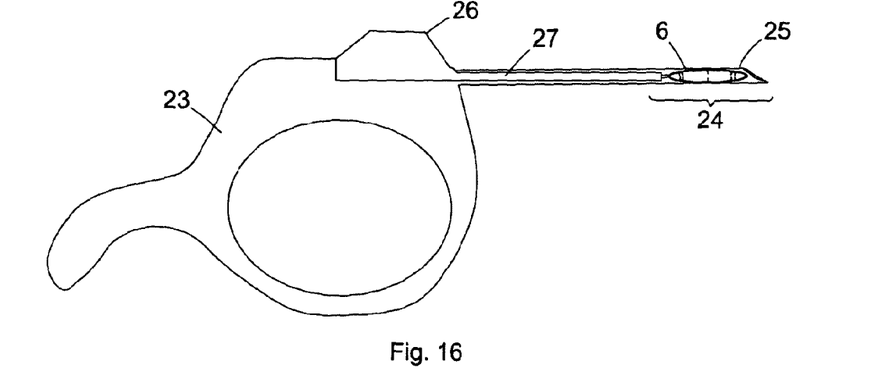
FIG. 16 shows a schematic diagram of an applicator comprising a catheter for inserting the wire scaffold into the ear.

The applicator comprises a handle (23) a portion (24) comprising the catheter (25) and scaffold (6) and a slider (26) to deploy the scaffold. The slider comprises a portion (27) which fits inside the catheter and can be moved manually forwards thereby releasing the scaffold from the catheter.

Figure 17:
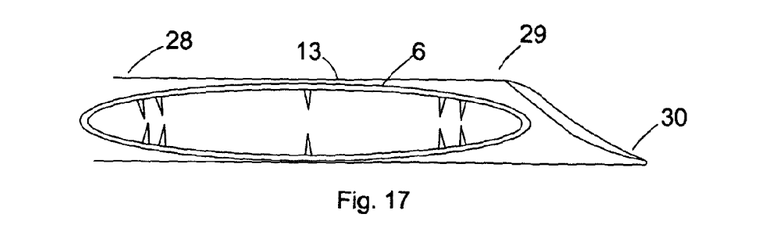
FIG. 17 shows an enlargement of the portion comprising the catheter with the wire scaffold inserted in the catheter.

An enlarged diagram of the catheter is shown in FIG. 17. The catheter contains the scaffold (6) in its compressed first configuration and comprises a proximal (28) and distal end (29) with a sharpened tip (30) at the distal end to effect insertion of the scaffold into the sub-dermal layer.

The catheter has a diameter which accommodates the scaffold in its compressed first configuration. The diameter is at least 0.3 mm although it may be 1.0 mm or 1.5 mm or even up to 3 mm. In one embodiment the diameter is typically in the range of 0.3 mm to 1.0 mm. If the diameter of the wires increases then the diameter of the delivery catheter will need to increase as well.

The catheter may be made of a solid material or a flexible material. The solid material may be selected from steel. The flexible material may be selected from silicone rubber, latex, teflon and thermoplastic elastomers. Preferably the material is inert and does not cause an adverse reaction with human tissue. For example, the catheter is made of steel.

The handle is designed such that a finger may be inserted through the handle to grip the applicator.

In another aspect of the present invention there is provided a method of treatment for reshaping the ear using the scaffold, comprising the steps of inserting at least one scaffold into the ear to be corrected, wherein the scaffold transforms from a first configuration to a second pre-programmed configuration, wherein the second pre-programmed configuration is in the shape of a horseshoe.

A according to a further aspect of the invention when the scaffold is in the form of a wire there is provided a method for re-shaping the ear, comprising the steps of inserting a scaffold into the ear to be corrected using a catheter wherein the scaffold transforms from a first configuration to a second pre-programmed configuration.

In one embodiment the second pre-programmed configuration is in the shape of a semi-circle or horseshoe.

The wire scaffold may be inserted into the ear in accordance with the following steps;
a) compressing the scaffold in its first configuration and inserting into the lumen of the catheter,
b) externally marking on the skin the desired position for insertion,
c) making a small incision in the skin,
d) inserting the catheter containing the scaffold under the skin following the path of the markings, or where the scaffold comprises engaging members, creating a sub-dermal space to accommodate the scaffold in its pre-programmed configuration and then inserting the scaffold,
e) moving the slider forwards such that the scaffold is deployed and adopts its second pre-programmed configuration,
f) removing the applicator.

Figure 12A:
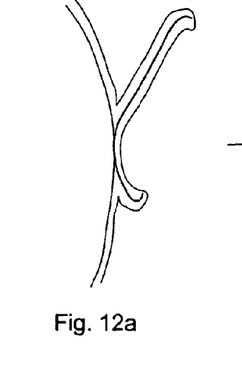
FIGS. 12a and 12b show a cross section of the shape of the cartilaginous portion of the ear before and after insertion of the scaffold.
Figure 12B:
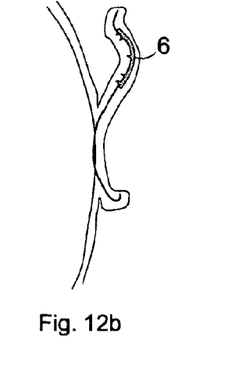

The shape of the ear is modified upon the scaffold adopting its second pre-programmed configuration (FIGS. 12a and 12b).

This method has the advantage that for both alternatives of step d), the method of insertion using a catheter based delivery is simplified and minimally invasive.

The method is additionally advantageous when the scaffold does not comprise any engaging members. In this embodiment there is no need to create a space or gap between the cartilage and sub-dermal layer prior to insertion of the scaffold. Upon insertion the scaffold creates an "interference fit" between the cartilage and sub-dermal layer as it expands into its second pre-programmed configuration. Consequently the scaffold is less likely to become dislodged due to the absence of an excess gap or space surrounding the scaffold. Furthermore the scaffold is held securely in position by the overlying skin.

The scaffold is removed from the ear by either cutting through the wire and removing by extracting as a single length through the incision, or by creating a larger incision in the skin and removing the scaffold in its second pre-programmed configuration. For example, the scaffold is removed in its second pre-programmed configuration.

In one embodiment of the method when the scaffold is in the form of a wire, the scaffold transforms from a first configuration to a second pre-programmed configuration and forms an "interference fit" between the cartilage and sub-dermal layer.

According to a further aspect of the invention when the scaffold is formed of a thermoplastic pliable material, there is provided a method for reshaping the ear using the scaffold of the invention. The method may comprise moulding the scaffold in vivo such that heat is applied to the scaffold once inserted into the sub dermal layer or moulding the scaffold prior to insertion in the sub dermal layer.

The method may comprise the steps of immersing the scaffold in water at a predefined temperature, placing the scaffold over the region of the ear to be corrected and moulding to the desired shape and inserting the cooled rigid scaffold in the sub-dermal layer. This method has the advantage that there is no heat damage to surrounding tissues during the application of heat and/or cooling of the scaffold.

Alternatively the method comprises the steps of inserting the scaffold in its rigid form into the sub dermal layer, applying heat to the scaffold in situ such that the scaffold transforms to a flexible, pliable state and moulding to the desired shape. The scaffold cools and becomes rigid thereby correcting the shape of the ear. This method has the advantage that it is not necessary for the engaging members to be of a different composition to the scaffold. The scaffold is fixed in position prior to the application of heat and remains in position when cooled.

The scaffold may be moulded manually or using a specific device. For example the scaffold is moulded manually.

The method may be a cosmetic method. For the avoidance of doubt all the methods referred to herein may be cosmetic.

The method may be a method in which the scaffold is inserted into the subcutaneous cartilaginous portion of the ear.

Typically, the method is for reshaping the anti-helical fold of the ear.

One or more scaffolds may be inserted into the ear depending on the deformity to be corrected. For example, between 1 and 4 scaffolds are inserted. In a further example, one or two scaffolds are inserted.

The scaffold may be inserted with an applicator.

REFERENCES

1. Alexander K. S., Stott D. J., Sivakumar B. and Kang N. A morphometric study of the human ear. J Plast Reconstr Aesthet Surg 2010;
2. Janz B. A., Cole P., Hollier L. H., Jr. and Stal S. Treatment of prominent and constricted ear anomalies. Plast Reconstr Surg 2009; 124; 27e-37e.
3. Bulstrode N. W., Huang S, and Martin D. L. Otoplasty by percutaneous anterior scoring. Another twist to the story: a long-term study of 114 patients. Br J Plast Surg 2003; 56; 1459.
4. Firmin F., Sanger C. and O'Toole G. Ear reconstruction following severe complications of otoplasty. J Plast Reconstr Aesthet Surg 2008; 61 Suppl 1; S13-20.
5. Furnas D. W. Complications of surgery of the external ear. Clin Plast Surg 1990; 17; 305-18.

6. Jeffery S. L. Complications following correction of prominent ears: an audit review of 122 cases. Br J Plast Surg 1999; 52; 588-90.
7. Tan S. T., Abramson D. L., MacDonald D. M. and Mulliken J. B. Molding therapy for infants with deformational auricular anomalies. Ann Plast Surg 1997; 38; 263-8.
8. Ullmann Y., Blazer S., Ramon Y., Blumenfeld I. and Paled I. J. Early nonsurgical correction of congenital auricular deformities. Plast Reconstr Surg 2002; 109; 907-13.
9. Sorribes M. M. and Tos M. Nonsurgical treatment of prominent ears with the Aurl method. Arch Otolaryngol Head Neck Surg 2002; 128; 1369-76.
10. Iatrou I, Theologie-Lygidakis N, Tzerbos F, Alexandridis K. The use of biodegradable plates in oral and maxillofacial surgery in children. The XVIIIth Congress of the European Association for Cranio-Maxillofacial Surgery, Barcelona, Spain, Sep. 12-15, 2006.
11. Nieminen T, Rantala I, Hiidenheimo I, Keranen J, Kainulainen H, Wuolijoki E, Kallela I. Degradative and mechanical properties of a novel resorbable plating system during a 3-year follow-up in vivo and in vitro. J Mater Sci: Mater Med 19:1155-1163, 2008.

EXAMPLES

Example 1

Radius of Curvature

Studies were carried out in human cadavers comparing scaffolds formed of shape memory material with varying radii of curvature. The scaffolds were not in the wire form. The dimensions of the scaffolds are shown in Table 1.

TABLE 1

| Scaffold | Scaffold Length (mm) | Bend radius (mm) | Tangent length (mm) |
| --- | --- | --- | --- |
| 1 | 10.0 | 3 | 0 |
| 2 | 13.3 | 4 | 0 |
| 3 | 16.6 | 5 | 0 |
| 4 | 19.9 | 6 | 0 |
| 5 | 14.6 | 3 | 2.3 |
| 6 | 17.9 | 4 | 2.3 |
| 7 | 21.2 | 5 | 2.3 |
| 8 | 24.5 | 6 | 2.3 |

Scaffolds 1-4 were semi-circular in shape and did not have tangential extensions.

Scaffolds 5-8 were of a horseshoe shape and comprised tangential extensions of the same length, but varying bend radius and overall length.

The inventors found that optimum configuration of the scaffold to the cartilage and correction of the antihelical fold was achieved when the bend radius was between 4 mm and 5 mm and a tangent length was present. If the shape of the scaffold is too acute at the apex i.e. when the overall length is long and the bend radius is below 4, then this causes the scaffold to sit 'proud' of the cartilage resulting sub-optimal conformance.

The invention claimed is:
1. A scaffold for reshaping the cartilaginous portion of an ear, the scaffold comprising engaging members and being formed from a shape memory material which transforms from a first, substantially planar configuration to a second, horseshoe shaped, pre-programmed configuration, wherein the scaffold is resiliently biased in the second pre-programmed configuration and comprises tangential extensions, wherein said horseshoe shaped configuration is a U shape defined by two tangential extensions arranged either inclined toward a central axis through the middle of the U shape to define a tapered configuration or in a parallel configuration, and wherein said engaging members project substantially perpendicular from the tangential extensions.

2. The scaffold of claim 1 configured to conform to the shape of the antihelical fold of an ear.

3. The scaffold according to claim 1 wherein said tangential extensions are between 1 and 5 mm long.

4. The scaffold according to claim 1 wherein said tangential extensions are at least 1 mm long.

5. The scaffold according to claim 4 wherein the tangent length is 2.3 mm.

6. The scaffold according to claim 1 wherein the scaffold is at least 10 mm long, at least 1 mm wide and up to 2 mm thick.

7. The scaffold according to claim 1 wherein the scaffold has a radius of curvature which is at least 3 mm.

8. The scaffold according to claim 1 wherein said engaging members comprise four engaging members projecting substantially perpendicular from the tangential extensions.

9. The scaffold according to claim 1 wherein the engaging members are tines.

10. The scaffold according to claim 9 wherein the tines are cylindrical in shape.

11. The scaffold according to claim 1 wherein the scaffold is electropolished or passivated.

12. The scaffold of claim 1 wherein the engaging members comprise four engaging members positioned on the tangential extensions of the horseshoe shape.

13. The scaffold of claim 1 wherein the engaging members comprise four engaging members which are each at least 1 mm long and are positioned on the tangential extensions of the horseshoe shape, with two of said four engaging members on a first of the tangential extensions and two of said four engaging members on a second of the tangential extensions, wherein the two engaging members on the first tangential extension extend inwardly toward the two engaging members on the second tangential extensions, which also extend inwardly.

14. The scaffold of claim 1 wherein the engaging members comprise eight engaging members which are each at least 1 mm long and are positioned on the tangential extensions of the horseshoe shape, with four of said eight engaging members on a first of the tangential extensions and four of said eight engaging members on a second of the tangential extensions, wherein the four engaging members on the first tangential extension extend inwardly toward the four engaging members on the second tangential extensions, which also extend inwardly.

15. The scaffold according to claim 1 wherein the scaffold is gold plated.

16. The scaffold of claim 1 wherein the first substantially planar configuration is a flat rectangular shape having a length of at least 10 mm and a width of at least 1 mm.

17. A method for reshaping the ear comprising the steps of inserting at least one scaffold as defined in claim 1 into the ear to be corrected thereby altering the shape of the ear.

18. An applicator for inserting a scaffold for reshaping the cartilaginous portion of an ear, the scaffold comprising engaging members and being formed from a shape memory material which transforms from a first, substantially planar configuration to a second, horseshoe shaped, pre-programmed configuration, wherein the scaffold is resiliently biased in the second pre-programmed configuration and comprises tangential extensions, wherein said horseshoe shaped configuration is a U shape defined by two tangential extensions arranged either inclined toward a central axis through the middle of the U shape to define a tapered configuration or in a parallel configuration, and wherein said engaging members project substantially perpendicular from the tangential extensions, the applicator comprising;
- a handle,
- a retaining guide for holding the scaffold in the first, substantially planar configuration; and
- a deployment member for pushing the scaffold from the retaining guide to insert the scaffold into the ear, the deployment member having a free end provided with notches to receive a plurality of engaging members on the scaffold to prevent yawing movement of the scaffold during insertion.

* * * * *